United States Patent [19]

Engelfried et al.

[11] 3,935,245
[45] Jan. 27, 1976

[54] RADIOACTIVELY LABELED STEROID DERIVATIVES

[75] Inventors: Otto Engelfried; Bob Nieuweboer; Karl Petzoldt; Ulrich Kerb; Klaus Lübke, all of Berlin, Germany

[73] Assignee: Schering Aktiengesellschaft, Berlin and Bergkamen, Germany

[22] Filed: June 4, 1974

[21] Appl. No.: 476,279

[30] Foreign Application Priority Data
June 8, 1973  Germany............................ 2330159

[52] U.S. Cl.............................. 260/397.1; 424/238
[51] Int. Cl.²............................................ C07J 9/00
[58] Field of Search................................ 260/397.1

[56] References Cited
OTHER PUBLICATIONS

Barbieri et al., "Journ. Chromatogr." (1972) 69(1) 151–155 (Eng.) —abstract enclosed CA-16/77 (1972) p. 85, 145p.

Massaglia et al. "Int. J. Appl. Radiat. Isotopes" (1973) 24(8) 455–462 Abstract enclosed CA Vol. 79 (1973) p. 126754 y.

*Primary Examiner*—Elbert L. Roberts
*Attorney, Agent, or Firm*—Millen, Raptes & White

[57] ABSTRACT

Steroids bearing the substituent $-X-NR_1R_2$ wherein $-NR_1R_2$ is a tritium of carbon-14 labeled amino or amino-acid group and $-X-$ is $-R_3-$, $-OCOR_3-$, $=N-O-R_3-$ or $-NHCOR_3-$ wherein $R_3$ is $-(CH_2)_nCO-$ in which $n$ is 0–4, are useful as diagnostic agents.

16 Claims, No Drawings

RADIOACTIVELY LABELED STEROID DERIVATIVES

BACKGROUND OF THE INVENTION

This invention relates to steroids useful as diagnostic agents.

There is a need for accurate and highly sensitive analytical methods for active substances, for example, steroids, which can be present in extremely small quantities, in body fluids, e.g., blood, urine, etc. The analysis must respond, if at all possible, only to the specific active substance, a steroid. In other words, the analysis must be specific and not give false positives by the presence of other substances in the same sample of body fluid.

A plurality of analytical methods already exists which are based on a great variety of physicochemical processes, e.g., spectrometry, titrimetry, chromatography, etc. Because of the minute amounts of substances to be detected or detectable, immunological testing methods have gained increasing popularity in the determination of active substances, e.g., of steroids, since immunological testing methods, more specifically radioimmunological tests, are generally superior, due to their sensitivity and specificity, to other testing methods in the determination of active agents inherent in the body or similar active agents.

A prerequisite of a radioimmunological test is that a sufficiently specific antiserum must be available and the compound to be detected, or a suitable derivative thereof, must be available as a tracer in a maximally high radioactively marked form.

The production of a specific antiserum can be accomplished relatively easily if the antigen to be detected is itself capable of stimulating the formation of antibodies, i.e., it is also an immunogen. This holds true, inter alia, for all proteohormones which, in an extremely highly purified form, can be used directly for the production of suitable antisera. The problem becomes more complicated if the antigen is a low-molecular compound, such as a steroid, for example, which itself does not provoke an immune response, i.e., is not immunogenic.

In such cases, the linking of the low-molecular antigen, frequently also called haptene, e.g., a steroid, to a high-molecular carrier, and the use of this "conjugate" as immunogen has proven itself satisfactorily. However, a basic disadvantage of this process is that the linking of the haptene to the high-molecular carrier leads to a reduction in the specificity of the thus-obtained antibodies, as is the case in the majority of the antisera presently available. The loss in specificity manifests itself in the cross reactions of the antisera with other active substances, e.g., steroids, exhibiting characteristic functional groups similar to those of the steroid to be detected. This is due to the fact that the characteristic functional groups are employed for the linking of the haptene to the high-molecular carrier, so that the functional groups cannot take part as determinants during the stimulation of the antibody synthesis and thus cannot contribute to the specificity of the thus-formed antibodies.

Also, the above-mentioned second prerequisite, viz., the accessibility of sufficiently highly radioactively labeled tracers, is not fulfilled in many cases, especially in the case of steroids used as active substances so that in spite of the possibility of producing the desired antisera, radioimmunological determination of these steroids cannot be accomplished.

For this reason, highly radioactively labeled steroid derivatives, which are readily obtainable and can be used as tracers, would represent a substantial advance in the art of diagnostic agents.

The present invention now makes available radioactively tagged steroid derivatives which do not have the disadvantages described hereinabove.

SUMMARY OF THE INVENTION

The novel compounds of this invention are steroids bearing as a substituent group $-X-NR_1R_2$ wherein $-NR_1R_2$ is a tritium- or carbon-14 labeled amino or of an aminoacid radical; and X is $R_3$, $-O-CO-R_3$, $=N-O-R_3$ or $-NH-CO-R_3$, preferably at a position of the steroid skeleton which is otherwise unsubstituted, i.e., not occupied by a functional group or a substituent, wherein $R_3$ is $-(CH_2)_n-CO-$ and $n$ is an integer from 0 to 4, inclusive.

These steroids can be represented by the general Formula I

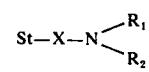

wherein St is a steroid moiety and $-X-NR_1R_2$ has the values given above.

In a process aspect, this invention relates to a process for the preparation of the steroid derivatives of Formula I.

In a method of use aspect, this invention relates to the use of the novel compounds of Formula I as diagnostic agents.

DETAILED DISCUSSION

The steroids of this invention are characterized by the presence thereon on the steroid nucleus or a 17-position side chain thereof of the group $-X-NR_1R_2$ preferably at a position not also occupied by a functional group. Such steroids can be represented by the general Formula II

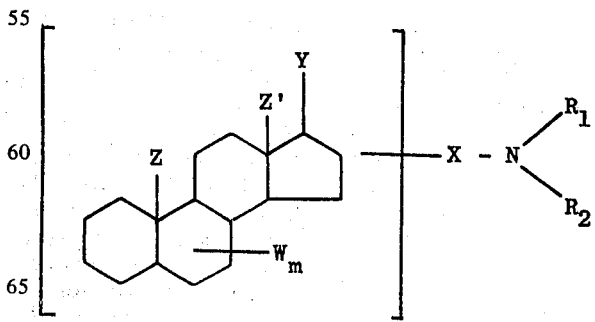

wherein
W is a steroid ring substituent and *m* is a positive integer, e.g., 1–6;
Z and Z' are angular methyl groups, one or both of which optionally are absent or replaced by another lower-alkyl group, e.g., ethyl;
X and —NR$_1$R$_2$ have the values given above; and
Y is a functional group at the 17-position.

The group —X—NR$_1$R$_2$ can be present on any of rings A, B, C and D of the steroid nucleus, or can be present on the side chain optionally present at the 17-position. The steroids represented by Formulae I and II ordinarily bear at least one additional functional group and/or substituent on one or more of rings A, D and/or on the optionally present side chain. The grouping —X—NR$_1$R$_2$ preferably is present at a position which lacks any other functional group or substituent, more preferably on the B-ring, at the 6- or 7-position, or on the C-ring, at the 11- or 12-position. Thus, if the B-ring or C-ring, respectively, bears another functional group or a substituent, then the grouping —X—NR$_1$R$_2$ preferably is at a different position of the C-ring or B-ring, respectively.

Examples of such additional functional groups or substituents are: keto groups at one or more of the 3-, 6-, 11-and/or 17-positions; free, esterified, or etherified hydroxy at one or more of the 1-, 3-, 6-, 11-, 16- and/or 17-positions; alkyl of 1–5 carbon atoms, preferably methyl or ethyl, at one or more of the 1-, 2-, 6-, 7-, 10-, 13- and/or 16-positions; methylene group at one or more of the 1,2-, 6,7-, 15,16- and/or 16,17-positions; and a halogen atom, preferably fluorine or chlorine, at one or more of the 2-, 4-, 6-, 7-, 9-, 11- and/or 16-positions.

Rings A, B, C and D can be saturated or unsaturated. For example, double bonds can be present at one or more of the 1(2)-, 3(4)-, 4(5)-, 5(6)-, 6(7)-, 5(10)-, 9(11)- and/or 16(17)-position.

Y can be any of the side chains of steroids of, e.g., the androstane, pregnane and cholane series. For example, Y can be an oxygen atom, free, etherified or esterified hydroxy, an optionally substituted aliphatic group of 1–8 carbon atoms, including acetyl, hydroxyacetyl or acyloxyacetyl, alone or in combination with hydroxy or acyloxy, alkyl or alkinyl group of up to 5 carbon atoms, hydroxy, alone or in combination with free, esterified or etherified alkoxy group up to 6 carbon atoms, alkoxycarbonyl of up to 11 carbon atoms and/or a saturated oxygen-heterocyclic group.

Examples of such steroids are those of the general Formula III

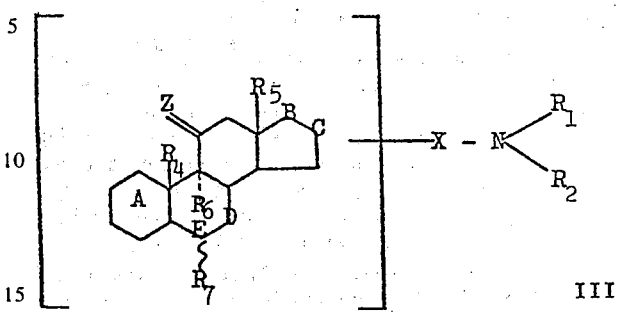

wherein —X—NR$_1$R$_2$ has the values given above; A is

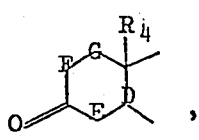 , 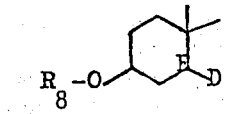 or 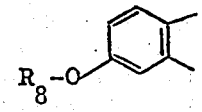 ;

B-C is 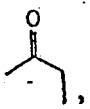 ,

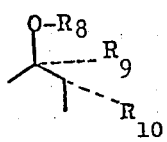 or 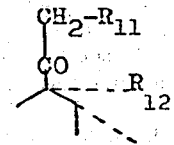 ;

Z is an oxygen atom, two hydrogen atoms or the grouping H,OH; E—D is a single or double bond; F—G is —CH$_2$—CH$_2$—, —CH=CH, —CH$_2$—CH(CH$_3$)—, —CH=C(CH$_3$)— or

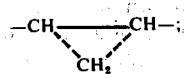

R$_4$ is a hydrogen atom or methyl; R$_5$ is methyl or ethyl; R$_6$ is a hydrogen, fluorine or chlorine atom; R$_7$ is a hydrogen, fluorine or chlorine atom or methyl; R$_8$ is a hydrogen atom or alkanoyl of up to 15 carbon atoms; R$_9$ is a hydrogen atom, methyl or ethinyl; R$_{10}$ is a hydrogen atom, methyl or —O—R$_8$; R$_{11}$ is a hydrogen atom, a halogen atom or —O—R$_8$; R$_{12}$ is a hydrogen atom or —O—R$_8$; R$_9$ and R$_{10}$ or R$_{10}$ and R$_{12}$ collectively are

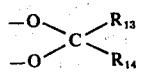

wherein R$_{13}$ and R$_{14}$ each are a hydrogen atom or alkyl of up to 5 carbon atoms.

Preferred steroids of Formula I are, inter alia, those of the general Formula IV

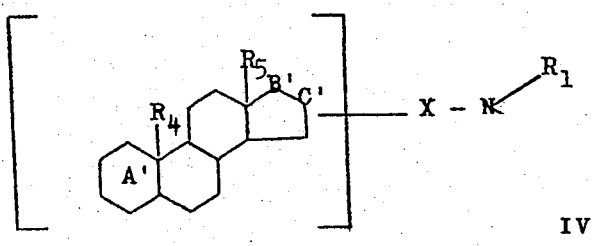

wherein —X—NR$_1$R$_2$ has the values given above and preferably is in the 6-, 7-, 11- or 12-position;

A' is

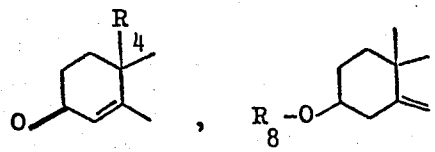 or 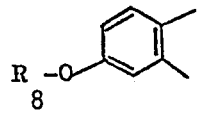

B'—C' is

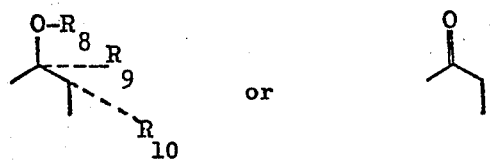

wherein R$_4$, R$_5$, R$_8$, R$_9$ and R$_{10}$ each have the values given above.

Further preferred steroids of Formula I are those of the general Formula V

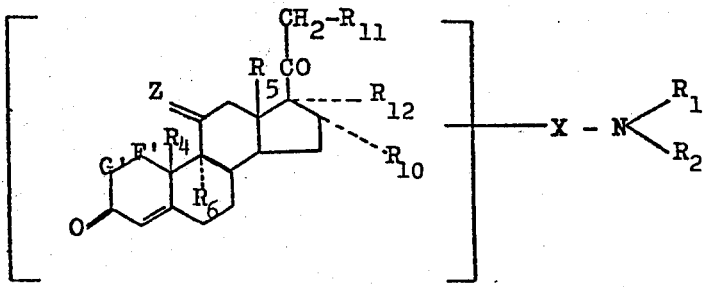

wherein —X—NR$_1$R$_2$ has the values given above and preferably in the 6- or 7-position; F'—G' is a single or double bond, and R$_4$, R$_5$, R$_6$, R$_{10}$, R$_{11}$, R$_{12}$ and Z each have the values given above.

Further preferred steroids are those of the general Formula VI

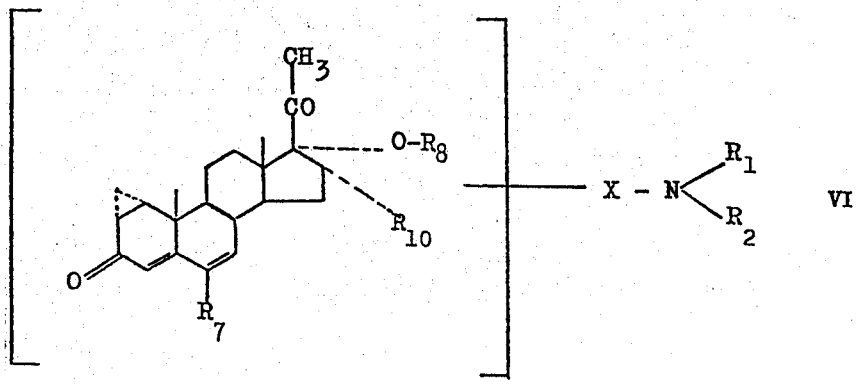

wherein —X—NR$_1$R$_2$ is preferably in the 11- or 12-position and, along with R$_7$, R$_8$ and R$_{10}$, has the values given above.

The steroids of general Formula I can be produced in a manner known per se from corresponding steroids of general Formula VII $$St - X - OH \qquad (VII),$$

wherein St and X have the values given above, optionally after conversion into the corresponding acid chloride, azide, azolide, anhydride or ester, by reaction with a compound of the general Formula VIII

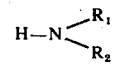    VIII wherein —NR$_1$R$_2$ has the values given above.

Preferred starting steroids are those otherwise corresponding to each of Formulae II, III, IV, V and VI but having an —X—OH group or a corresponding chloride, azide, azolide, anhydride or ester group, instead of an —X—NR$_1$R$_2$ group, wherein X has the values given above, e.g., those of the formulae St—R$_3$—OH, St—O—CO—R$_3$—OH, ST=N—O—R$_3$—OH and St—NH—CO—R$_3$—OH, or a corresponding chloride, azide, azolide, anhydride or ester group.

The steroids of general Formula VII can be reacted with the compounds of general Formula VIII according to methods as known to those skilled in the art, for example, from peptide chemistry, e.g., the method using mixed anhydrides, the carbodiimide method, the azide method and the method employing activated esters. A general description of these methods is found, inter alia, in H. Beyer, "Lehrbuch der organischen Chemie", S. Hirzel publishers, Leipzig (1968) pages 720–723.

In addition to the steroids whose preparation is specifically described hereinafter, the following are suitable starting steroids for producing the compounds of this invention:

6β-4'-carboxybutyrylamino-1.3.5(10)-estratriene-3,17β-diol,
6β-4'-carboxybutyrylamino-1.3.5(10)-estratriene-3,16α,17β-triol,
(3,20-dioxo-4-pregnen-6α-yl) hydrogen glutarate,
(17β-hydroxy-3-oxo-17α-ethinyl-4-estren-11α-yl)hydrogen glutarate,
(17β-hydroxy-3-oxo-18-methyl-17α-ethinyl-4-estren-6β-yl) hydrogen glutarate,
(6-chloro-17α-acetoxy-3,20-dioxo-1α,2α-methylene-4,6-pregnadien-11α-yl) hydrogen glutarate,
(6α-fluoro-11β-hydroxy-3,20-dioxo-16α-methyl-1,4-pregnadien-21-yl) hydrogen glutarate,
(1-methyl-3-oxo-5α-androst-1en-17β-yl) hydrogen glutarate,
(3β-heptanoyloxy-17-oxo-5-androsten-7α-yl) hydrogen glutarate,
(17β-hydroxy-3-oxo-18methyl-17α-ethinyl-4-estrene-6β-yl) hydrogen adipinate,
(3,20-dioxo-4-pregnen-6α-yl) hydrogen adipinate,
6β-5'-carboxypentanoylamino-1,3,5(10)-estratriene-3,16α,17β-triol,
(21-acetoxy-17α-hydroxy-3,11,20-trioxo-1,4-pregnadien-6β-yl) hydrogen succinate,
(21-acetoxy-17α-hydroxy-3,11,20-trioxo-1,4-pregnadien-7α-yl) hydrogen glutarate,
(21-acetoxy-17α-hydroxy-3,11,20-trioxo-4-pregnen-6β-yl) hydrogen adipinate,
(21-acetoxy-3,20-dioxo-4-pregnen-6β-yl) malonate,
(1α-methyl-17β-acetoxy-3-oxo-5α-androstan-6β-yl)hydrogen succinate,
(3β-acetoxy-20-oxo-5α-pregnan-12β-yl) hydrogen glutarate,
(3α-acetoxy-20-oxo-5β-pregnan-12α-yl) hydrogen succinate,
(17α-methyl-17β-propionyloxy-3-oxo-4-androsten-11α-yl) malonate.
6-2'-carboxyethoxyimino-17α-ethinyl-1,3,5(10)-estretriene-3,17β-diol,
6β-carboxy-5α-androstan-3,17β-diol.

Reacting these steroids which can be prepared according to the procedures of the illustrative preparations hereinafter with L-tyrosine, L-phenyl-alamine, histamine, dopamine, prolin, respectively according to the procedures of the Examples hereinafter produces N-[(3,17β-dihydroxy-1,3,5(10)-estratriene-6β-yl)-amino carbonylbutyryl]-L-tyrosine-[3,5-$^3$H$_2$],
N-[(3,16α,17β-trihydroxy-1,3,5(10)-estratriene-6β-yl)-amino carbonylbutyryl]-L-phenylalamine-[2,3-$^3$H$_2$],
N-[(3,20-dioxo-4-pregnen-6α-yl)-oxycarbonylbutyryl]-histamine-[2,5-$^3$H$_2$],
N-[(17β-hydroxy-3-oxo-17α-ethinyl-4-estren-11α-yl)-oxycarbonylbutyryl]-dopamin-[2,3-$^3$H$_2$],
N-[(17β-hydroxy-3-oxo-18-methyl-17α-ethinyl-4-estren-6β-yl)-oxycarbonylbutyryl]-prolin-[u-$^{14}$C],
N-[(6-chloro-17β-acetoxy-3,20-dioxo-1α,2α-methylen-4,6-pregnadien-21-yl)-oxycarbonylbutyryl]-L-tyrosine-[3,5-$^3$H$_2$],
N-[(6α-fluoro-11β-hydroxy-3,20-dioxo-16α-methyl-1,4-pregnadien-21-yl)-L-phenylalanin-[2,3-$^3$H$_2$],
N-[(1-methyl-3-oxo-5α-androst-1-en-17β-yl)-oxycarbonylbutyryl]-histamine-[2,5-$^3$H$_2$],
N-[(3β-heptanoyl-17-oxo-5-androsten-7α-yl)-oxycarbonylbutyryl]-dopamin-[2,3-$^3$H$_2$],
N-[(17β-hydroxy-3-oxo-18-methyl-17α-ethinyl-4-estren-6β-yl)-L-tyrosine-[3,5-$^3$H$_2$],
N-[(3,20-dioxo-4-pregnen-6α-yl)-oxycarbonylpentanoyl]-prolin-[u-$^{14}$C],
N-[(3,16α,17β-trihydroxy-1,3,5(10)-estratriene-6β-yl)-aminocarbonylpentanoyl]-histamine-[2,5-$^3$H$_2$],
N-[(21-acetoxy-17α-hydroxy-3,11,20-trioxo-1,4-pregnadien-7α-yl)-oxysuccinyl]-L-phenylalamine-[2,3-$^3$H$_2$],
N-[(21-acetoxy-17α-hydroxy-3,11,20-trioxo-1,4-pregnadien-7α-yl)-oxycarbonylbutyryl]-dopamin-[2,3-$^3$H$_2$],
N-[(21-acetoxy-17α-hydroxy-3,11,20-trioxo-4pregnen-6β-yl)-oxycarbonylpentanoyl]-histamin-[2,5-$^3$H$_2$],
N-[(21-acetoxy-3,20-dioxo-4-pregnen-6β-yl)-oxycarbonylacetyl]-L-tyrosine-[3,5-$^3$H$_2$],
N-[(1α-methyl-17β-acetoxy-3-oxo-5α-androstan-6β-yl)-oxysuccinyl]-L-phenylalanine-[2,3-$^3$H$_2$],
N-[(3β-acetoxy-20-oxo-5α-pregnan-12β-yl)-oxycarbonylbutyryl]-L-tyrosine-[3,5-$^3$H$_2$],
N-[(3α-acetoxy-20-oxo-5β-pregnan-12α-yl)-oxysuccinyl]-histamine-[2,5-$^3$H$_2$],
N-[(17α-methyl-17β-propionyloxy-3-oxo-4-androsten-11α-yl)-oxycarbonylacetyl]-prolin-[u-$^{14}$C],
N-[(3,17β-dihydroxy-17α-ethinyl-1,3,5(10)-estratriene-6-ylidene)-aminooxypropionyl]-dopamin-[2,3-$^3$H$_2$],
N-[(3,17β-dihydroxy-5α-androstan-6β-yl)-carbonyl]-histamin-[2,5-$^3$H$_2$], respectively.

Tritium- or carbon-14-labeled compounds bearing an amino group or groups which can be reacted with the starting steroids include primary amines, e.g., compounds of Formula VIII wherein $R_1$ is a hydrogen atom and $R_2$ is alkyl, which optionally is substituted, for example, by a hydroxy group or by a heterocyclic group. Included with such amines are alkylamines of 1–8, preferably 1 to 6, carbon atoms; cycloalkylamines wherein cycloalkyl is an unsubstituted or substituted cycloalkyl ring of, e.g., 3–8 ring members; aralkylamines of 7–13, preferably 7–10, carbon atoms and aryl is 1–2 separate or fused carbocyclic aromatic rings which are unsubstituted, e.g., phenyl, p-biphenyl, naphthyl, or bear one or more substituents, such as, for example, alkyl and alkoxy of 1–4 carbon atoms, carboxy, carbalkoxy wherein alkoxy is of 1–4 carbon atoms, cyano, halo, e.g., chloro, bromo and fluoro, trifluoromethyl, —$CONH_2$, CONHAlkyl and —CON(Alkyl)$_2$ wherein alkyl is of 1–4 carbon atoms, nitro and sulfato; and arylamines wherein aryl is as defined above.

Specific examples are methyl-, ethyl-, propyl-, butyl-, pentyl-, benzyl-, ph enylethyl-, phenylpropylamin, tyramin, tryptamine, serotonin, histamine, norepinephrine, guanine, adenine, cytosine and other biogenic amines.

Also suitable as starting amino compounds are secondary amines, e.g., compounds of Formula VIII wherein both $R_1$ and $R_2$ are optionally substituted alkyl, and cyclic amines, e.g., compounds of Formula VIII wherein $R_1$ and $R_2$ collectively are alkylene of 4–7 atoms which optionally is interrupted by a hetero atom, e.g., an oxygen, nitrogen of sulfur atom.

Examples of such secondary amines are dimethyl- and diethylamin, piperidine, epinephrin, purine bases, e.g., xanthine and its derivatives, N-methyl aminoacids, such as N-methyl glycine, N-methyl alanine, N-methyl valine, N-methyl leucine, N-methyl phenylalanine, N-methyl glutamine, N-methyl asparagine.

Also suitable as amino compounds are aliphatic and aromatic aminoacids, e.g., compounds of Formula VIII wherein $R_1$ is a hydrogen atom and $R_2$ is the remainder of an amino acid. Examples of such aminoacids are glycine, alanine, valine, isoleucine, leucine, phenylalanine, tyrosine, thyroxine, L-dopa, β-alanine, ε-aminocaproic acid, γ-amino butyric acid, serin, threonine, methionine, asparagine, glutamine.

Further suitable as amino compounds are heterocyclic amino acids, e.g., compounds of Formula VIII wherein $-NR_1R_2$ is the amino radical of a heterocyclic aminoacid, such as, for example, proline, hydroxyproline, tryptophan and histidine. The level of tritium labeling amounts to 1–4 $^3H$ per molecule of the starting amino compounds, one to about all of the carbon atoms of the starting compounds may be $^{14}C$ labeled.

Compounds of Formula VIII are sufficiently readily available commercially in highly radioactivated form, or can be conveniently produced, so that the radioactivated steroids of Formula I can be easily produced in a minimum amount of time.

In general, the thus-produced steroids of Formula I are not isolated but instead are used in the test in the form of their solutions.

The above-described radioactive tracers, i.e., compounds of general Formula I, are substituted in an analogous manner for the steroid conjugates utilized for the antibody production. They can be used as such in radioimmunological tests, i.e., they are diagnostic agents. In contrast to processes known from the literature, which use as the tracer the entire immunogen (i.e., a steroid — highly polymeric carrier conjugate) and introduce the radioactivity by means of iodation, the tracers of general Formula I described herein have the advantage that such antibodies directed against antigenic determinants of the carrier do not have any effect on the test result. The specificity of the test is thus still further increased. Consequently, these tracers are suitable for the detection and measurement of extremely minor amounts of the steroids up to a range of a picogram/ml. ($1 \times 10^{-12}$ g/ml).

Many of the starting steroids of general Formula VII are known and can be obtained according to processes generally known to a person skilled in the art. Thus, for example, it is possible to prepare the compounds of Formula VII wherein X is $-O-CO-R_3$ or $-NH-CO-R_3$ by reacting the corresponding hydroxy or amino steroid with the cyclic anhydride of a dicarboxylic acid, such as, for example, succinic acid, glutaric acid, adipic acid anhydride.

The novel compounds will be used as diagnostic agents as known in the art, e.g., in Steroids 18 (1971) 605–620 or J. Clin. Endocr. 32 (1971) 619–624. An illustrative example is as follows:

Radioimmunoassay of norethisterone (NET=17β-hydroxy-17α-ethinyl-4-estren-3-one) in plasma

| Reagents | |
| --- | --- |
| Buffer: | phosphate buffer (50 mM, pH 7,5) containing sodiumchloride (0.15 M), merthiolate $^{(R)}$ (0,01 % w/v) and human serum albumin (0.5 % w/v) |
| Diethylether: | distilled over ferrous sulphate |
| Dextran-coated charcoal: | 0.5 % (w/v) charcoal (Norit A) and 0.05 % (w/v) dextran (Dextran T-70, Pharmacia) in buffer. The suspension is stirred for 1 h and can be stored at 4° C. |
| | N-[17α-ethinyl-17β-hydroxy-3-oxo-4-estren-11α-yloxysuccinyl]-L-tyrosine-[3,5-$^3H_2$] (ex 3) specific activity: 30–60 Ci/mMol Take 10 μl of the eluate from example 3 and evaporate the solvent. Add enough buffer (about 20 ml) to achieve a radioactive concentration of 200 000 dpm/ml. |
| NET: | Schering AG, Berlin |
| Anti-NET-serum: | The antibody was raised in rabbits by immunizing with norethisterone-11α-hemisuccinate-bovine serum albumin. The dilution of the antiserum used in the assay is such that it will bind approx. 60 % of the added $^3H$-compound in the absence of non-radioactive NET. |

PROCEDURE 2,250 cpm of ex 3 in 20 μl methanol are pipetted into glass tubes containing a suitable volume of plasma for extraction (those with less than 500 μl are made up to that volume with distilled water) and into two extra tubes containing 500 μl distilled water (water blanks). Diethylether (2 ml) is added to each tube and the contents shaken for approximately 10 min.

The tubes are placed in a freezer for approximately 30 min. to solidify the aqueous phase and the ether extracts are decanted into disposable glass tubes. The solvent is evaporated with a stream of nitrogen and 1 ml of buffer is added to the dried extract. The tubes are aggitated on a vortex mixer and allowed to incubate at 37° C for a period of 15 min. An aliquot (800 μl) is taken from each tube and counted in a liquid scintillation counter for evaluation of the procedural losses.

40 μl of the buffer solution and 60 μl buffer are pipetted into assay tubes (12 mm × 75 mm disposable glass tubes). A standard curve is set up by adding 100 μl buffer containing 500 pg, 400 pg, 300 pg, 200 pg, 100 pg, 50 pg, 25 pg, 12.5 pg and 0 pg NET, respectively to assay tubes.

| Assay scheme | | | |
|---|---|---|---|
| Total radio-activity (RA; 2 tubes) | charcoal blank (CO; 2 tubes) | Standard curve | sample |
| 100 μl buffer | 100 μl buffer | 100 μg buffer containing standard | 40 μl extract in buffer 60 μl buffer |
| + | + | + | + |
| 200 μl buffer | 200μl buffer | 200 μl anti-NET-serum | 200 μl anti-NET-serum |
| | incubate at 37° C for 15 Min. | | |
| + | + | + | + |
| 100 μl ex 3 = 22,000 dpm in buffer | 100 μl ex 3 = 22,000 dpm in buffer | 100 μl ex 3 = 22,000 dpm in buffer | 100 μl ex 3 = 22,000 dpm in buffer |

The tubes are aggitated on a vortex and left overnight (approx. 16 hours) at 4° C.

After incubation the tubes are placed in crushed ice and to each tube (except for the RA-tubes) 100 μl of buffer and 500 μl of dextran coated charcoal are added. To the RA tubes 600 μl of buffer are added. The tubes are aggitated on a vortex mixer, left for 15 min at 0° C and centrifuged at 3000 rpm for 15 min in a refrigerated centrifuge at 4° C. Following centrifugation, the tubes are kept at 0° C and 500 μl of supernatant is transferred into a counting vial. 10 ml scintillation fluid is added and the samples are counted.

CALCULATION OF THE RESULTS

The percentage of binding for each sample is calculated from the cpm of the sample and the cpm of the total radioactivity added (RA). For the standard curve percentage of binding is plotted versus pg amount of NET.

The NET concentrations in each of the unknowns may then be read directly from the graph.

The following are illustrative preparations of the starting steroids of Formula VII.

$A_1$ 21.3 g. of 6-ketoestradiol diacetate — prepared from 6-ketoestradiol-17-acetate (Belgian Patent No. 785,448) by usual acetylation — is reacted under Reformatskii conditions with 29 ml. of ethyl bromoacetate. The crude product is mixed with silica gel, introduced into a silica gel column, and eluted with a hexane-ethyl acetate mixture. The fractions which are uniform according to thin-layer chromatography are evaporated. The residue is refluxed with 450 ml. of alcohol after adding a mixture of 40 ml. of alcohol and 4.5 ml. of concentrated sulfuric acid for 4 hours. The mixture is concentrated, precipitated into ice water, filtered off, and washed neutral. After fractional crystallization of the crude product (9.1 g.) from ethyl acetate and chromatography of the mother liquor, 4.0 g. of 6-ethoxycarbonylmethyl-1,3,5(10),6-estratetraene-3,17β-diol is obtained, m.p. 178°/179°–180.5° C., as well as 1.2 g. of 6-ethoxycarbonylmethylene-1,3,5(10)-estratriene-3,17β-diol, m.p. 181°/182°–183.5° C.

20 g. of 6-ethoxycarbonylmethyl-1,3,5(10),6-estratetraene-3,17β-diol is hydrogenated in 280 ml. of tetrahydrofuran and 280 ml. of methanol in the presence of 2 g. of Pd/CaCO₃ (10%) until 1 millimole of hydrogen has been absorbed per millimole of substance. The thus-obtained product is 6β-ethoxycarbonylmethyl-1,3,5(10)-estratriene-3,17β-diol as a foamy mass. The same compound is also produced by the analogous hydrogenation of 6-ethoxycarbonylmethylene-1,3,5(10)-estratriene-3,17β-diol. The preparation of 6β-ethoxycarbonylmethyl-1,3,5(10)-estratriene-3,17β-diol can be simplified by hydrolyzing the crude product of the Reformatskii reaction, freeing the thus-obtained hydrolyzate from by-products by fractional filtration over silica gel, and hydrogenating the evolved mixture of 6-ethoxycarbonylmethyl-1,3,5(10),6-estratetraene-3,17β-diol and 6-ethoxycarbonylmethylene-1,3,5(10)-estratriene-3,17β-diol as indicated above.

8.0 g. of 6β-ethoxycarbonylmethyl-1,3,5(10)-estratriene-3,17β-diol is refluxed for 3 hours with 180 ml. of N/2 potassium hydroxide solution. The mixture is then precipitated into ice water, neutralized, and extracted repeatedly with ether. The ether extracts are extracted several times with dilute soda solution, and the soda extracts are acidified with hydrochloric acid. The precipitate is filtered off and washed neutral, thus obtaining 4.14 g. of 6β-carboxymethyl-1,3,5(10)-estratriene-3,17β-diol, m.p. 220.5°–222° C. (acetone).

$A_2$ 1.4 g. of 6β-ethoxycarbonylmethyl-1,3,5(10)-estratriene-3,17β-diol — produced according to $A_1$ — is subjected to an Oppenauer oxidation with cyclohexanone and aluminum isopropylate. After chromatography on silica gel, 1.0 g. of 3-hydroxy-6β-ethoxycarbonylmethyl-1,3,5(10)-estratrien-17-one is obtained (m.p. 137.5°–138° C.) which is converted, by alkaline saponification with potassium hydroxide solution, analogously to $A_1$, into 3-hydroxy-6β-carboxymethyl-1,3,5(10)-estratrien-17-one, m.p. 240°–242° C. (acetone).

The same compound is also produced when conducting the oxidation with Jones reagent and working up the reaction product analogously.

$A_3$ a. 10.0 g. of 3-hydroxy-6β-ethoxycarbonylmethyl-1,3,5(10)-estratrien-17-one — produced in accordance with $A_2$ — is acetylated with 20 ml. of acetic anhydride in 20 ml. of pyridine for 20 hours at room temperature. After precipitation into ice water, filtration, and taking up the precipitate in methylene chloride, the reaction product is dried and evaporated, thus obtaining 11.8 g. of 3-acetoxy-6β-ethoxycarbonylmethyl-1,3,5(10) estratrien-17-one, which is heated to the boiling point with 140 ml. of isopropenyl acetate in the presence of 1.4 g. of p-toluenesulfonic acid and then subjected to a slow distillation. The cooled reaction product is diluted with methylene chloride and washed with sodium bicarbonate solution and water, dried, and evaporated, thus resulting in 13.3 g. of a crude product. After chromatography on silica gel, pure 3,17-diacetoxy-6β-ethoxycarbonylmethyl-1,3,5(10),16-estratetraene is obtained as an almost colorless oil.

Five grams of 3,17-diacetoxy-6β-ethoxycarbonylmethyl-1,3,5(10),16-estratetraene is dissolved in 75 ml. of benzene and, after the addition of 3.2 g. of m-chloroperbenzoic acid, agitated at room temperature for 90 minutes under nitrogen. The mixture is then diluted with benzene, repeatedly extracted with dilute soda solution, and washed neutral with water. After drying of the solution and evaporation of the solvent, 3,17β-diacetoxy-16α,17-epoxy-6β-ethoxycarbonylmethyl-1,3,5(10)-estratriene is obtained which, without purification, is treated for 30 minutes with 2.0 ml. of perchloric acid (70% strength) in glacial acetic acid at room temperature. After dilution with methylene chloride, the reaction mixture is washed successively with water, dilute soda solution, and water, dried, and evaporated. The subsequent chromatography on silica gel yields 1.95 g. of 3,16α-diacetoxy-6β-ethoxycarbonylmethyl-1,3,5(10)-estratrien-17-one as an oil.

300 mg. of 3,16α-diacetoxy-6β-ethoxycarbonylmethyl-1,3,5(10)-estratrien-17-one is dissolved in 11 ml. of methanol and gradually combined at +5°C. with 0.17 g. of NaBH$_4$ in 9 ml. of methanol. After allowing the mixture to stand for 20 hours at room temperature, it is concentrated and stirred into water which contains hydrochloric acid. The reduction product is taken up in ethyl acetate, the solution is washed neutral, dried, and evaporated. By preparative thin-layer chromatography, 330 mg. of crude product yields 16α-acetoxy-6β-ethoxycarbonylmethyl-1,3,5(10)-estratriene-3,17β-diol, m.p. 170.5°–171.5°C. and 6β-ethoxycarbonylmethyl-1,3,5(10)-estratriene-3,16α,17β-triol, m.p. 192.5°–193°C.

100 mg. of the above crude product is refluxed with 4 ml. of N/2 potassium hydroxide solution for 2 hours. The mixture is then introduced into ice water, neutralized, and extracted with ether. The ether extracts are extracted with dilute soda solution, and the soda extracts are acidified with hydrochloric acid. After filtration and washing the mixture neutral, 25 mg. of 6β-carboxymethyl-1,3,5(10)-estratriene-3,16α,17β-triol is obtained, m.p. 259°–262°C.

b. Two grams of 6-ketoestriol acetate — produced according to Biochem. J. 74 (1960) 430 — are reacted analogously to A$_1$ under Reformatskii conditions with 3 ml. of ethyl bromoacetate and worked up. The crude product is hydrolyzed, the hydrolyzate is separated from by-products and hydrogenated. The subsequent saponification with potassium hydroxide solution yields, after working up the reaction product, 300 mg. of 6β-carboxymethyl-1,3,5(10)-estratriene-3,16α,17β-triol.

A$_4$ 2.0 g. of 3-hydroxy-6β-ethoxycarbonylmethyl-1,3,5(10)-estratrien-17-one — prepared according to A$_2$ — is introduced into a suspension of 1.1 g. of potassium tert.-butylate in 20 ml. of tetrahydrofuran, into which was previously introduced acetylene at −5° C. for 1 hour. Acetylene is introduced for another 3 hours at −5° C., and then the reaction mixture is decomposed by adding 65 ml. of 20% strength sulfuric acid and 35 ml. of water. The mixture is suction-filtered from the potassium sulfate, the filtrate is concentrated under vacuum, taken up in methylene chloride, the methylene chloride phase is washed neutral, and concentrated to dryness. The residue is recrystallized from methylene chloride, resulting in 1.4 g. of 17α-ethinyl-6β-carboxymethyl-1,3,5(10)-estratriene-3,17β-diol, m.p. 226.5°–229°C.

A$_5$

A mixture of 2.24 g. of 3.17β-dihydroxy-17α-ethinyl-1,3,5(10)-estratrien-6-one — produced according to Belgian Patent No. 785,448 — 3.0 g. of sodium acetate, 1.96 g. of carboxymethoxylamine hemihydrochloride sicc., 54.0 ml. of ethanol, and 6 ml. of water is heated to the boiling point for 1 hour. Under cold conditions, 360 ml. of ether is added thereto; then, the reaction mixture is extracted three times with respectively 60 ml. of 5% soda solution saturated in sodium bicarbonate. The aqueous phase is acidified with 30 ml. of concentrated hydrochloric acid and the thus-precipitated, smeary substance is taken up in ethyl acetate; the aqueous phase is twice extracted with ethyl acetate. The ethyl acetate phases are washed three times with water, dried, and evaporated. The residue is recrystallized from ethyl acetate, thus obtaining 3.1 g. of 6-carboxymethoxyimino-17α-ethinyl-1,3,5(10)-estratriene-3,17β-diol (with 1 mole of crystallized ethyl acetate), m.p. 80°–88°C. (decomposition).

The same compound is produced from 17-hydroxy-3-acetoxy-17α-ethinyl-1,3,5(10)-estratrien-6-one, m.p. 181.5°–185°C. — prepared from the 3,17-dihydroxy compound by partial acetylation — by an analogous reaction.

A$_6$ 4.4 g. of 17β-acetoxy-6-oximino-1,3,5(10)-estratrien-3-ol, m.p. 252° C. (decomposition) — produced from 6-ketoestradiol diacetate according to Ann. 692 (66) 180 — is reduced with sodium in isopropanol to the corresponding amino compound. The methanolic solution of the crude base is mixed with ethereal hydrogen chloride. The hydrochloride crude product yields, after repeated redissolution from methanol, pure (3,17β-dihydroxy-1,3,5(10)-estratrien-6β-yl) ammonium chloride, m.p. 251° C. (decomposition); 100 mg. of this product is reacted for 20 hours at room temperature with 40 mg. of succinic acid anhydride and 0.77 ml. of N-ethylmorpholine (as a 1% pyridine solution). Yield: 100 mg. of 6β-3'-carboxypropionylamino-1,3,5(10)-estratriene-3,17β-diol, m.p. 157°C. (decomposition).

A$_7$ 3.5 g. of 16α, 17β-diacetoxy-6-oximino-1,3,5(10)-estratrien-3-ol — produced from 6-ketoestriol triacetate according to Biochem. J. 74 (1960) 430 and A$_6$ — is reduced as described in A$_6$ and reacted to the (3,16α,17β-trihydroxy-1,3,5(10)-estratrien-6β-yl) ammonium chloride, of which 100 mg. is reacted with 40 mg. of succinic acid anhydride and 0.77 ml. of N-ethylmorpholine, thus obtaining 85 mg. of 6β-3'-carboxypropionylamino-1,3,5(10)-estratriene-3,16α,17β-triol.

A$_8$

Two grams of 6α-hydroxyprogesterone is refluxed for 1 hour in 20 ml. of pyridine with 4 g. of succinic acid anhydride. After cooling, the solution is stirred into ice water and acidified with 1N hydrochloric acid. The smeary precipitation product is separated and dissolved in methylene chloride; the solution is washed with hydrochloric acid and water and evaporated under vacuum. The residue (2.57 g. of foam) is dissolved in methanol, combined with carbon, filtered, and the filtrate concentrated under vacuum. By trituration of the residue with pentane, 2.1 g. of amorphous (3,20-dioxo-4-pregnen-6α-yl) hydrogen succinate is produced. UV: $\epsilon_{238} = 14,100$.

$A_9$ 2.82 g. of 11α-hydroxy-17α-ethinyl-19-nortestosterone is heated with 18 ml. of pyridine and 1.35 g. of succinic acid anhydride for 20 hours on a steam bath. The mixture is poured into water and extracted with methylene chloride. The methylene chloride extracts are extracted exhaustively with soda solution (5% strength), and the combined soda extracts are acidified with hydrochloric acid. The thus-separated product is taken up in methylene chloride and washed neutral. After evaporation of the solvent, the crude hemisuccinate remains in the form of a foam. For additional purification, the product is dissolved in methylene chloride and repeatedly extracted with soda solution. The combined soda extracts are acidified and the thus-separated, smeary product is taken up in methylene chloride and washed neutral. Yield: 1.9 g. of (17β-hydroxy-3-oxo-17α-ethinyl-4-estren-11α-yl) hydrogen succinate. UV: $\epsilon_{239} = 15,700$.

$A_{10}$ 720 mg. of 6β,17β-dihydroxy-18-methyl-17α-ethinyl-4-estren-3-one — produced from 17β-hydroxy-18-methyl-17α-ethinyl-4-estren-3-one by microbiological hydroxylation as described in the following paragraph — is reacted analogously to $A_9$ with succinic acid anhydride and worked up, the reaction time being shortened to 5 hours. The hydrogen succinate, purified by way of the sodium salt, is triturated with ether/hexane. After the solvent has been evaporated, 430 mg. of (17β-hydroxy-3-oxo-18-methyl-17α-ethinyl-4-estren-6β-yl) hydrogen succinate is obtained, m.p. 111°/143° C. (decomposition). UV: $\epsilon_{235} = 11,900$.

A glass fermenter having a capacity of 50 liters is filled with 29 l. of a liquid, sterile nutrient medium having the following composition: 3% glucose, 1% corn steep, 0.2% $NaNO_3$, 0.1% $KH_2PO_4$, 0.2% $K_2HPO_4$, 0.05% $MgSO_4$, 0.002% $FeSO_4$, and 0.05% KCl. Then, the fermenter is inoculated with 1 liter of a subculture of the strain *Mucor griseocyanus* (ATCC 1207b), grown for 2 ½ days. After a growth period of 12 hours, 6 g. of 17β-hydroxy-18-methyl-17α-ethinyl-4-estren-3-one, dissolved in 75 ml. of dimethylformamide, is added thereto. After further, incubating for 60 hours, the content of the fermenter is collected, filtered, extracted with methyl isobutyl ketone, the extract evaporated to dryness, and the residue is purified by chromatography on silica gel. After crystallization from ethyl acetate/isopropyl ether, 6β,17β-dihydroxy-18-methyl-17α-ethinyl-4-estren-3-one is obtained, m.p. 194°–195° C.

$A_{11}$ 0.433 g. of 6-chloro-11α-hydroxy-17-acetoxy-1α,2α-methylene-4,6-pregnadiene-3,20-dione — prepared from 6-chloro-17-acetoxy-1α,2α-methylene-4,6-pregnadiene-3,20-dione by microbiological hydroxylation as described in the following paragraph — is reacted analogously to $A_9$ with succinic acid anhydride and worked up. After purification by way of the sodium salt, 230 mg. of (6-chloro-17-acetoxy-3,20-dioxo-1α,2α-methylene-4,6-pregnadien-11α-yl) hydrogen succinate is obtained as a foam. UV: $\epsilon_{280} = 15,500$.

A glass fermenter having a capacity of 50 liters is filled with 29 l. of a liquid, sterile nutrient medium having the following composition: 3% glucose, 1% corn steep, 0.2% $NaNO_3$, 0.1% $KH_2PO_4$, 0.2% $K_2HPO_4$, 0.05% $MgSO_4$, 0.002% $FeSO_4$, 0.05% KCl. Thereafter, the charge is inoculated with 1 liter of a 72-hour subculture of *Glomerella cingulata* (ATCC 10 534). After an initial growth phase of 12 hours, the substrate is added in the form of an aseptically filtered solution of 6 g. of 6-chloro-17-acetoxy-1α,2α-methylene-4,6-pregnadiene-3,20-dione in 150 ml. of dimethylformamide. After 37 hours, the culture broth is filtered, the filtrate is extracted with methyl isobutyl ketone, the extract is evaporated to dryness under vacuum, and the remaining residue is purified by chromatography on a silica gel column, thus obtaining 6-chloro-11α-hydroxy-17-acetoxy-1α,2α-methylene-4,6-pregnadiene-3,20-dione, m.p. 133°–136° C.

$A_{12}$

Two grams of 7α-hydroxy-4-androstene-3,17-dione — prepared from 4-androstene-3,17-dione by microbiological hydroxylation as described in the following paragraph — is ethinylated analogously to $A_4$. The thus-obtained 7α,17β-dihydroxy-17α-ethinyl-4-androsten-3-one, m.p. 220–221° C., is reacted analogously to $A_9$ with 0.8 g. of succinic acid anhydride and worked up, thus obtaining (17β-hydroxy-3-oxo-17α-ethinyl-4-androsten-7α-yl) hydrogen succinate as a foam. UV: $\epsilon_{240} = 16,800$ (methanol).

Four glass fermenters, each having a capacity of 50 l., are charged with respectively 29 l. of a liquid nutrient medium, consisting of 10% liquid glucose and 2% corn steep, and sterilized with steam. Thereafter, the fermenters are inoculated with 1 l. of a subculture, grown for 34 hours, of the strain *Absidia orchidis* (ATCC No. 6811). After a growth period of 12 hours, each fermenter is additionally charged with an aseptically filtered solution of 6 g. of 4-androstene-3,17-dione in 200 ml. of dimethylformamide. After a contact period of 36 hours, the fermentation is interrupted, the culture broth is filtered, the culture filtrate is exhausted with methyl isobutyl ketone and extracted. The combined organic phases are evaporated to dryness under vacuum. The remaining residue is crystallized twice from acetone, whereby concomitantly produced 6β-hydroxy-androstenedione is caused to remain in the mother liquor and can thus be separated. The product is 7α-hydroxy-4-androstene-3,17-dione (3.12 g.), m.p. 239.8° C.

$A_{13}$

Five grams of 6α-fluoro-11β,21-dihydroxy-16α-methyl-1,4-pregnadiene-3,20-dione is refluxed in 25 ml. of pyridine with 5 g. of succinic acid anhydride for 2 hours. After cooling to 20°C., the solution is stirred into ice water, acidified with hydrochloric acid, and the thus-precipitated product is vacuumfiltered, washed with water, and dried. By recrystallization from ethyl acetate, 4.85 g. of (6α-fluoro-11β-hydroxy-3,20-dioxo-16α-methyl-1,4-pregnadien-21-yl) hydrogen succinate is obtained, m.p. 212°–214° C.

$A_{14}$ 8.9 g. of 1-methyl-17β-hydroxy-5α-androst-1-en-3-one is dissolved in 53 ml. of pyridine and refluxed for 3.5 hours after adding 8.9 g. of succinic acid anhydride. After the reaction mixture has been worked up as described in $A_{13}$, (1-methyl-3-oxo-5α-androst-1-en-17β-yl) hydrogen succinate is produced, m.p. 149°–150° C. (ethyl acetate/hexane). Yield: 85% of theory.

$A_{15}$

A solution of 2 g. of 3β-heptanoyloxy-5-androstene-7,17-dione 17-ethylene ketal in 240 ml. of methanol and 100 ml. of THF is gradually combined at room temperature with 600 mg. of $NaBH_4$ and agitated for 30 minutes at room temperature under $N_2$. The charge is neutralized with glacial acetic acid, concentrated, taken up in ether, washed neutral with saturated NaCl solution, dried, and evaporated. The residue is treated under heating with acetic acid to split the ketal. The thus-obtained 3β-heptanoyloxy-7α-hydroxy-5-androsten-17-one is converted analogously to $A_9$ into (3β-heptanoyloxy-17-oxo-5-androsten-7α-yl) hydrogen succinate. Yield: 450 mg.

The compounds of this invention are utilized as diagnostic agents; they are customarily used in the form of solutions. Advantageously, the compounds are put to use in the solutions in which they are obtained during their preparation. However, this does not exclude the possibility of mixing the solutions with other solvents or of taking up the compounds of this invention, after isolation, in other solvents and using them in this form.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

1.0 μmol of 6β-carboxymethyl-1,3,5(10)-estratriene-3,17β-diol and 1.0 μmol of N-ethylmorpholine are dissolved at −15° to −20°C. in 2 ml. of peroxide-free tetrahydrofuran. To this solution is added 1.1 μmol of isobutyl chlorocarbonate, and the solution is then maintained at −5° to −10°C. for 15–20 minutes. The above mixture is combined with 0.1 μmol of [3,5-$^3H_2$]-L-tyrosine hydrochloride and 0.2 μmol of N-ethylmorpholine, which two latter compounds had been taken up in 150 μl. of water. The reaction mixture is maintained at 0°C. for 2–3 hours. Then, the reaction solution is introduced into a silica gel column and eluted with an ethyl acetate/methanol gradient. The eluate is collected in fractions of 2 ml. The identification of the fractions, containing the thus-formed N-[3,17β-dihydroxy-1,3,5(10)-estratrien-6β-yl)-acetyl] L-tyrosine-[3,5-$^3H_2$] is carried out by measuring the radioactivity and the UV absorption.

EXAMPLE 2

Analogously to Example 1, N-[(17α-ethinyl-3,17β-dihydroxy-1,3,5(10)-estratrien-6β-yl)-acetyl]-L-tyrosine-[3,5-$^3H_2$] is obtained from 17α-ethinyl-6β-carboxymethyl-1,3,5(10)-estratriene-3,17β-diol and [3,5-$^3H_2$]-L-tyrosine hydrochloride.

EXAMPLE 3

Analogously to Example 1, N-[17α-ethinyl-17β-hydroxy-3-oxo-4-estren-11α-yloxysuccinyl]-L-tyrosine-[3,5-$^3H_2$] is produced from (17β-hydroxy-3-oxo-17α-ethinyl-4-estren-11α-yl) hydrogen succinate and [3,5-$^3H_2$]-L-tyrosine hydrochloride.

EXAMPLE 4

Analogously to Example 1, N-[17α-acetoxy-6-chloro-1α,2α-methylene-3,20-dioxo-4,6-pregnadien-11α-yloxysuccinyl]-L-tyrosine-[3,5-$^3H_2$] is obtained from (6-chloro-17-acetoxy-3,20-dioxo-1α,2α-methylene-4,6-pregnadien-11α-yl) hydrogen succinate and [3,5-$^3H_2$]-L-tyrosine hydrochloride.

EXAMPLE 5

2 μmol of 6β-(3-carboxypropionylamino)-1,3,5(10)-estratriene-3,17β-diol and 2 μmol of N-ethylmorpholine are dissolved at −10° to −15°C. in 3 ml. of dimethylformamide. 2.2 μmol of ethylchlorocarbonate is added to this solution, and the latter is then maintained at −5°C. for 10–15 minutes. 0.2 μmol of [2,3-$^3H_2$]-L-phenylalanine is taken up in 220 μl. of $10^{-3}$ N NaOH and added to the above mixture of substances. The reaction charge is maintained at about +4°C. overnight, and the thus-formed N-[(3,17β-dihydroxy-1,3,5(10)-estratrien-6β-yl)-aminosuccinyl]-L-phenylalanine-[2,3-$^3H_2$] is eluted by chromatography on a silica gel column with an ethyl acetate/methanol gradient. The corresponding fractions are identified by UV absorption and measurement of the radioactivity.

EXAMPLE 6

Analogously to Example 5, N-[1-methyl-3-oxo-5α-androst-1-en-17β-yloxysuccinyl]-L-phenylalanine-[2,3-$^3H_2$] is obtained from (1-methyl-3-oxo-5α-androst-1-en-17β-yl) hydrogen succinate and [2,3-$^3H_2$]-L-phenylalanine.

EXAMPLE 7

1.5 μmol of 3-hydroxy-6β-carboxymethyl-1,3,5(10)-estratrien-17-one and 1.6 μmol of triethylamine are dissolved at −15° to −20°C. in 3 ml. of peroxide-free tetrahydrofuran. To this solution is added 1.6 μmol of isobutyl chlorocarbonate, and the solution is then maintained at −5° to − °C. for 5 minutes. 0.2 μmol of [2,5-$^3H_2$]-histamine dihydrochloride and 0.4 μmol of triethylamine are taken up in 200 μl. of water and added to the aforementioned mixture of substances. The reaction mixture is maintained at 0° to −5°C. for 2 hours. Thereafter, the thus-formed N-[(3-hydroxy-17-oxo-1,3,5(10)-estratrien-6β-yl)-acetyl]-histamine-[2,5-$^3H_2$] is obtained in solution, as described above, by chromatography over a silica gel column.

EXAMPLE 8

Analogously to Example 7, N-[17α-ethinyl-17β-hydroxy-18-methyl-3-oxo-4-estren-6β-yloxysuccinyl]-histamine-[2,5-$^3H_2$] is obtained from (17β-hydroxy-3-oxo-18-methyl-17α-ethinyl-4-estren-6β-yl) hydrogen succinate and [2,5-$^3H_2$]-histamine dihydrochloride.

EXAMPLE 9

1 μmol of 6β-carboxymethyl-1,3,5(10)-estratriene-3,16α,17β-triol and 1 μmol of N-ethylmorpholine are dissolved at −15° to −20°C. in 2 ml. of dimethyl sulfoxide. To this solution is added 1 μmol of isobutyl chlorocarbonate, and the solution is then maintained at −5°C. for 5 minutes. 0.1 μmol of [μ-$^{14}C$]-proline and 0.1 μmol of N-ethylmorpholine are taken up in 100 μl. of water and added to the above-mentioned substance mixture. The reaction mixture is maintained at 0°C. overnight. The thus-formed N-[(3,16α,17β-trihydroxy-1,3,5(10)-estratrien-6β-yl)-acetyl]-proline-[μ-$^{14}$C] is then obtained in a solution, as described above.

EXAMPLE 10

Analogously to Example 9, N-[3,20-dioxo-4-pregnen-6α-yloxysuccinyl]-proline-[μ-$^{14}$C] is obtained from (3,20-dioxo-4-pregnen-6α-yl) hydrogen succinate and [μ-$^{14}$C]-proline.

EXAMPLE 11

Analogously to Example 9, N-[3β-heptanoyloxy-17-oxo-5-androsten-7α-yloxysuccinyl]-proline-[μ-$^{14}$C] is produced from (3β-heptanoyloxy-17-oxo-5-androsten-7α-yl) hydrogen succinate and [μ-$^{14}$C]-proline.

EXAMPLE 12

2 μmol of 6-carboxymethoxyimino-17α-ethinyl-1,3,5(10)-estratriene-3,17β-diol and 2 μmol of N-ethylmorpholine are dissolved at −20° to −25°C. in 3 ml. of peroxide-free tetrahydrofuran. To this solution is added 1.9 μmol of isobutyl chlorocarbonate, and the solution is then maintained at −5°C. for 5–8 minutes. 0.3 μmol of [2,3-$^3$H$_2$]-dopamine hydrochloride and 0.3 μmol of N-ethylmorpholine are taken up in 200 μl. of water and added to the above mixture of substances. The reaction mixture is maintained at −5°C. for 4 hours and the thus-formed N-[(17α-ethinyl-3,17β-dihydroxy-1,3,5(10)-estratrien-6-ylidene)-amino-oxyacetyl]-dopamine-[2,3-$^3$H$_2$] is obtained as described in the above examples.

EXAMPLE 13

Analogously to Example 12, N-[6α-fluoro-11β-hydroxy-16α-methyl-3,20-dioxo-1,4-pregnadien-21-yloxysuccinyl]-dopamine-[2,3-$^3$H$_2$] is produced from (6α-fluoro-11β-hydroxy-3,20-dioxo-16α-methyl-1,4-pregnadien-21-yl) hydrogen succinate and [2,3-$^3$H$_2$]-dopamine hydrochloride.

EXAMPLE 14

1.0 μmol of 6β-(3-carboxypropionyl)-amino-1,3,5(10)-estratriene-3,16α,17β-triol and 1.1 μmol of N-ethylmorpholine are dissolved at −15°C. to −20°C. in 2 ml. of peroxide-free tetrahydrofuran. To this solution is added 1.0 μmol of isobutyl chlorocarbonate, and the solution is then maintained at −5°C. for 5–10 minutes. 0.1 μmol of [4,5-$^3$H$_2$]-L-leucine and 0.1 μmol of N-ethylmorpholine are taken up in 100μl. of water and added to the above mixture of substances. The reaction mixture is maintained at 0° to −5°C. for 5–6 hours. Thereafter, the thus-formed N-[(3,16α,17β-trihydroxy-1,3,5(10)-estratrien-6β-yl)-aminosuccinyl]-L-leucine-[4,5-$^3$H$_2$] is obtained in solution by means of chromatography on a silica gel column, as described above.

EXAMPLE 15

Analogously to Example 14, N-[17α-ethinyl-17β-hydroxy-3-oxo-4-androsten-7α-yloxysuccinyl]-L-leucine-[3,5-$^3$H$_2$] is obtained from (17β-hydroxy-3-oxo-17α-ethinyl-4-androsten-7α-yl) hydrogen succinate and [3,5-$^3$H$_2$]-L-leucine.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. a radioactive labeled steroid bearing the radical —X—N—R$_1$R$_2$ wherein —NR$_1$R$_2$ is a tritium- or carbon-14 labeled amino or aminoacid radical and X is R$_3$, —O—CO—R$_3$, =N—O—R$_3$ or —NH—CO—R$_3$ wherein R$_3$ is —(CH$_2$)$_n$—CO— in which n is an integer from 0 to 4, inclusive.

2. The compound of claim 1, N-[(3,17β-dihydroxy-1,3,5(10)-estratriene-6β-yl)-acetyl]-L-tyrosine-[3,5-$^3$H$_2$].

3. The compound of claim 1, N-[(17α-ethinyl-3,17β-dihydroxy-1,3,5(10)-estratriene-6β-yl)-acetyl]-L-tyrosine-[3,5-$^3$H$_2$].

4. The compound of claim 1, N-[17α-ethinyl-17β-hydroxy-3-oxo-4-estren-11α-yloxysuccinyl]-L-tyrosine-[3,5-$^3$H$_2$].

5. The compound of claim 1 N-[17α-acetoxy-6-chloro-1α,2α-methylene-3,20-dioxo-4,6-pregnadien-11α-yloxysuccinyl]-L-tyrosine-[3,5-$^3$H$_2$].

6. The compound of claim 1, N-[(3,17β-dihydroxy-1,3,5(10)-estratrien-6β-yl)-aminosuccinyl]-L-phenylalanine[2,3-$^3$H$_2$].

7. The compound of claim 1, N-[1-methyl-3-oxo-5α-androst-1-en-17β-yloxysuccinyl]-L-phenylalanine-[2,3-$^3$H$_2$].

8. The compound of claim 1, N-[(3-hydroxy-17-oxo-1,3,5(10)-estratrien-6β-yl)-acetyl]-histamine-[2,5-$^3$H$_2$].

9. The compound of claim 1, N-[17α-ethinyl-17β-hydroxy-18-methyl-3-oxo-4-estren-6β-yloxysuccinyl]-histamine-[2,5-$^3$H$_2$].

10. The compound of claim 1, N-[(3,16α,17β-trihydroxy-1,3,5(10)-estratrien-6β-yl)-acetyl]-proline-[μ-$^{14}$C].

11. The compound of claim 1, N-[3,20-dioxo-4-pregnen-6α-yloxysuccinyl]-proline-[μ-$^{14}$C].

12. The compound of claim 1, N-[3β-heptanoyloxy-17-oxo-5-androsten-7α-yloxysuccinyl]-proline-[μ-$^{14}$C].

13. The compound of claim 1, N-[( α-ethinyl-3,17β-dihydroxy-1,3,5(10)-estratrien-6-ylidene)-amino-oxyacetyl]-dopamine-[2,3-$^3$H$_2$].

14. The compound of claim 1, N-[6α-fluoro-11β-hydroxy-16α-methyl-3,20-dioxo-1,4-pregnadien-21-yloxysuccinyl]-dopamine-[2,3-$^3$H$_2$].

15. The compound of claim 1, N-[(3,16α,17β-trihydroxy-1,3,5(10)-estratrien-6β-yl)-aminosuccinyl]-L-leucine-[4,5-$^3$H$_2$].

16. The compound of claim 1, N-[17α-ethinyl-17β-hydroxy-3-oxo-4-androsten-7α-yloxysuccinyl]-L-leucine-[3,5-$^3$H$_2$].

\* \* \* \* \*